US00PP37793P2

(12) United States Plant Patent
Heuger

(10) Patent No.: US PP37,793 P2
(45) Date of Patent: Oct. 20, 2026

(54) ***HELLEBORUS* PLANT NAMED 'HL 1056'**

(50) Latin Name: ***Helleborus* x *niger* X *Helleborus* x *hybridus***
Varietal Denomination: HL 1056

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 0 days.

(21) Appl. No.: 19/397,959

(22) Filed: Nov. 23, 2025

(51) Int. Cl.
*A01H 6/72* (2018.01)
*A01H 5/02* (2018.01)

(52) U.S. Cl.
USPC ..... Plt./439

(58) Field of Classification Search
USPC ..... Plt./439
CPC ..... A01H 6/72; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Helleborus* plant named 'HL 1056', characterized by its upright to outwardly spreading and mounded plant habit; moderately vigorous growth habit; dark green-colored leaflets; freely flowering habit; flowers with white and purplish red bi-colored sepals; and good garden performance.

2 Drawing Sheets

Figure 1:
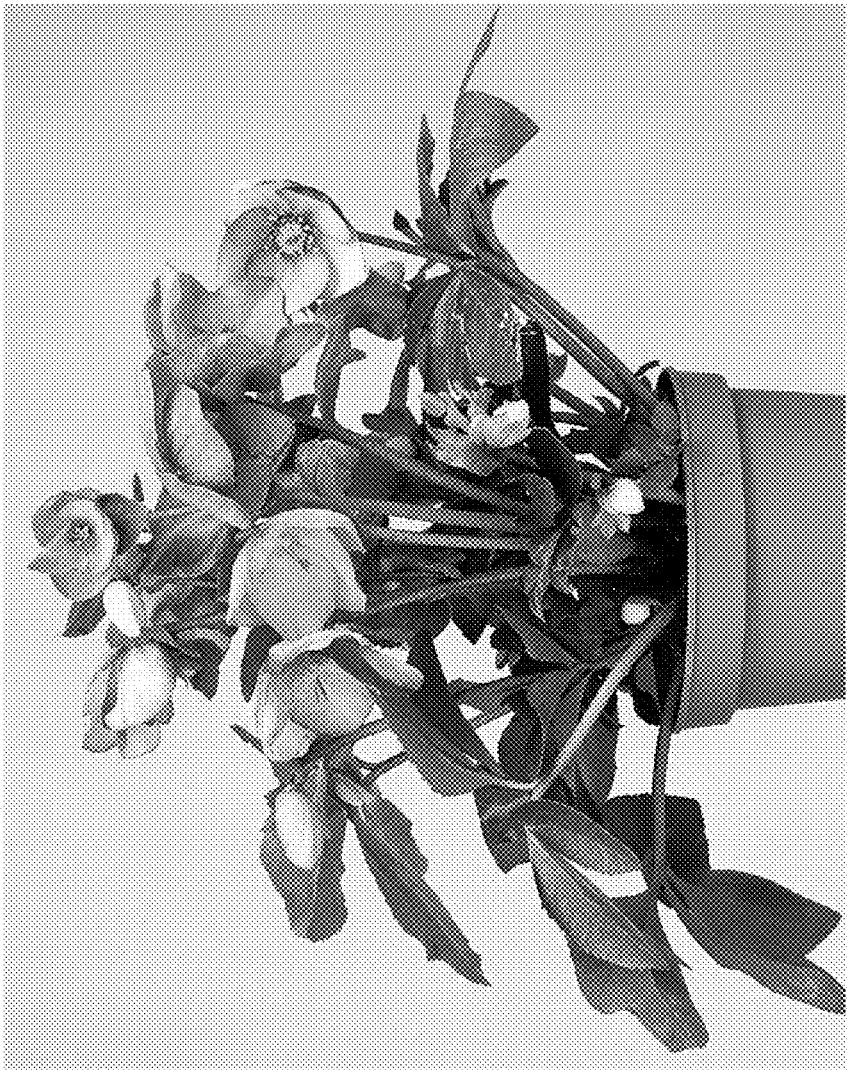

Botanical designation: *Helleborus* x *niger* X *Helleborus* x *hybridus*.

Cultivar denomination: 'HL 1056'.

CROSS-REFERENCED TO CLOSELY-RELATED APPLICATIONS

A European Community Plant Breeder's Rights application for the instant plant was filed by the Inventor/Applicant, Mr. Josef Heuger of Glandorf, Germany, on Nov. 30, 2024, application number 2024/2903. Foreign priority is not claimed to this application.

A United Kingdom Plant Breeder's Rights application for the instant plant was filed by the Inventor/Applicant, Mr. Josef Heuger of Glandorf, Germany, on Aug. 29, 2025, application number 30/993. Foreign priority is not claimed to this application.

BACKGROUND OF THE INVENTION

The present invention relates to a new and distinct cultivar of *Helleborus* plant, botanically known as *Helleborus* x *niger* X *Helleborus* x *hybridus* and hereinafter referred to by the name 'HL 1056'.

The new *Helleborus* plant is a product of a planned breeding program conducted by the Inventor in Glandorf, Germany. The objective of the breeding program was to create new uniform *Helleborus* plants with unique leaf and flower coloration and tolerance to biotic and abiotic stresses.

The new *Helleborus* plant originated from a cross-pollination conducted by the Inventor in Glandorf, Germany in November, 2016 of a proprietary selection of *Helleborus* x *niger* identified as code number 01.0661, not patented, as the female, or seed, parent and a proprietary selection of *Helleborus* x *hybridus* identified as code number 16-23, not patented, as the male, or pollen, parent. The new *Helleborus* plant was discovered and selected by the Inventor as a single flowering plant from within the progeny of the stated cross-pollination grown in a controlled greenhouse environment in Glandorf, Germany in November, 2018.

Asexual reproduction of the new *Helleborus* plant by in vitro axillary meristem culture in a controlled environment in Glandorf, Germany since September, 2019 has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'HL 1056'. These characteristics in combination distinguish 'HL 1056' as a new and distinct *Helleborus* plant:

1. Upright to outwardly spreading and mounded plant habit.
2. Moderately vigorous growth habit.
3. Dark green-colored leaflets.
4. Freely flowering habit.
5. Flowers with white and purplish red bi-colored sepals.
6. Good garden performance.

Plants of the new *Helleborus* differ from plants of the female parent selection in the following characteristics:

1. Leaflets of plants of the new *Helleborus* are darker green in color than leaflets of plants of the female parent selection.
2. Flower sepals of plants of the new *Helleborus* are white and purplish red bi-colored whereas flower sepals of plants of the female parent selection are white in color.

Plants of the new *Helleborus* differ from plants of the male parent selection in the following characteristics:

1. Leaflets of plants of the new *Helleborus* are lighter green in color than leaflets of plants of the male parent selection.
2. Flower sepals of plants of the new *Helleborus* are white and purplish red bi-colored whereas flower sepals of plants of the male parent selection are pink in color.

Plants of the new *Helleborus* can also be compared to plants of *Helleborus* x *niger* X *Helleborus* x *hybridus* 'HL 1010', disclosed in U.S. Plant Pat. No. 34,932. In side-by-side comparisons, plants of the new *Helleborus* differ primarily from plants of 'HL 1010' in the following characteristics:

1. Leaflets of plants of the new *Helleborus* are lighter green in color than leaflets of plants of 'HL 1010'.
2. Flower sepals of plants of the new *Helleborus* are white and purplish red bi-colored whereas flower sepals of plants of 'HL 1010' are solid purplish red in color.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet (FIG. 1) is a side perspective view of a typical flowering plant of 'HL 1056' grown in a container.

Figure 2:
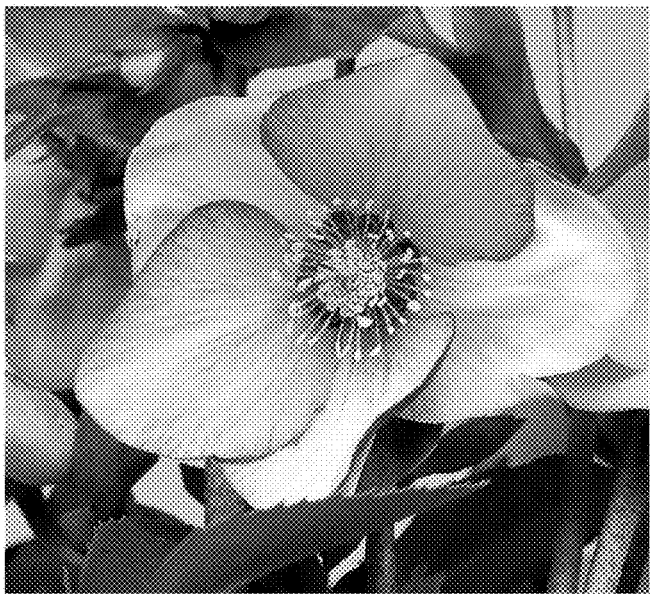

The photograph at the top of the second sheet (FIG. 2) is a close-up view of a typical flower of 'HL 1056'.

Figure 3:
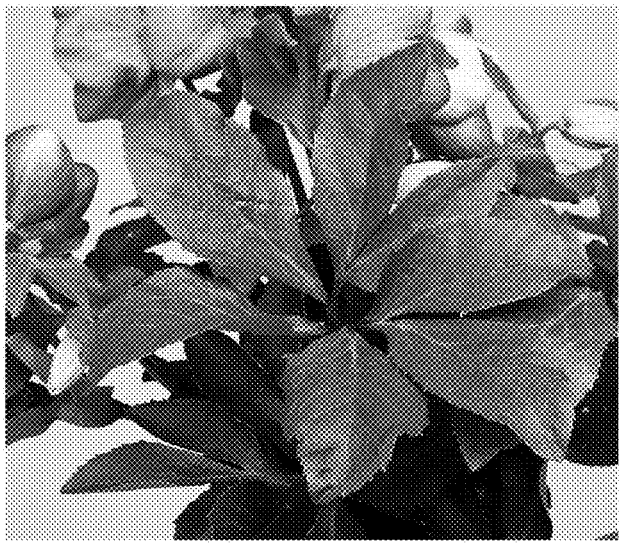

The photograph at the bottom of the second sheet (FIG. 3) is a close-up view of typical leaflets of 'HL 1056'.

DETAILED BOTANICAL DESCRIPTION

The aforementioned photographs and following observations, measurements and values describe plants grown during the winter in 17-cm containers in a glass-covered greenhouse in Glandorf, Germany and under cultural practices typical of commercial *Helleborus* production. During the production of the plants, day temperatures ranged from 12° C. to 32° C. and night temperatures ranged from 5° C. to 12° C. Plants were 48 weeks old when the photographs were taken and 14 months old when the detailed description was taken. In the following description, color references are made to The Royal Horticultural Society Colour Chart, Sixth Edition (2019 reprint), except where general terms of ordinary dictionary significance are used.

Botanical classification: *Helleborus* x *niger* X *Helleborus* x *hybridus* 'HL 1056'.

Parentage:

*Female, or seed, parent*.—Proprietary selection of *Helleborus* x *niger* identified as code number 01.0661, not patented.

*Male, or pollen, parent*.—Proprietary selection of *Helleborus* x *hybridus* identified as code number 16-23, not patented.

Propagation:

*Type*.—In vitro axillary meristem culture.

*Time to initiate roots, winter*.—About 55 days at temperatures about 12° C.

*Time to produce a rooted young plant, winter*.—About 170 days at temperatures ranging from about 4° C. to 15° C.

*Root description*.—Thick to thin, fleshy; typically white to brownish in color, actual color of the roots is dependent on substrate composition, water quality, fertilizer type and formulation, substrate temperature and physiological age of roots.

*Rooting habit*.—Low branching; sparse.

Plant description:

*Plant and growth habit*.—Herbaceous perennial; upright to outwardly spreading and mounding plant habit with flowers held above the foliar plane; plant shape, roughly flattened globular to globular; moderately vigorous growth habit and moderate growth rate.

*Plant height, soil level to top of foliar plane*.—About 25 cm.

*Plant height, soil level to top of flowers*.—About 25.7 cm.

*Plant diameter* (*area of spread*).—About 42.3 cm.

Leaf description:

*Arrangement*.—Leaves arranged in a basal rosette; leaves palmately compound with typically five leaflets per leaf.

*Leaf length*.—About 17.8 cm.

*Leaf width*.—About 19.5 cm.

*Leaflet length*.—About 11.1 cm.

*Leaflet width*.—About 6 cm.

*Leaf shape*.—Palmate; roughly reniform in outline.

*Leaflet shape*.—Elliptic to elliptic-ovate; lowest leaflets are occasionally cleft.

*Leaflet apex*.—Acute.

*Leaflet base*.—Attenuate.

*Leaflet margin*.—Serrate; coarsely undulate.

*Leaflet texture and luster, upper and lower surfaces*.—Smooth, glabrous; coriaceous and tough; slightly to moderately glossy.

*Leaflet venation pattern*.—Pinnate and reticulate.

*Leaflet color*.—Developing leaflets, upper surface: Close to 137A and 137B; at the base, tinged with close to N186C. Developing leaflets, lower surface: Close to 147B. Fully developed leaflets, upper surface: Close to a blend of 139A and 147A; at the base, tinged with close to 200A; venation, close to 144A. Fully developed leaflets, lower surface: Close to 147B; venation, close to 147B.

*Petioles*.—Length: About 17.2 cm. Diameter: About 6.5 mm by 7 mm. Strength: Strong. Texture and luster, upper and lower surfaces: Smooth, glabrous; slightly glossy. Color, upper and lower surfaces: Close to 144A with dots, close to N186C.

Flower description:

*Flower shape and habit*.—Single rotate bowl-shaped flowers arranged in panicles; freely flowering habit with about three flowers per inflorescence and about 39 flowers and flower buds per plant; flowers face outwardly to slightly nodding.

*Fragrance*.—None detected.

*Natural flowering season*.—Plants begin flowering about ten months after planting; plants flower naturally from early winter into the late winter in Germany.

*Flower longevity on the plant*.—About ten days; sepals persistent, other flower parts are not persistent.

*Flower buds*.—Length: About 2.8 cm. Diameter: About 1.5 cm. Shape: Ovate. Texture and luster: Smooth, glabrous; matte. Color: Close to 157A; at the base, fine dots, close to 185D; margins, tinged with close to 185B.

*Inflorescence height* (*including peduncle*).—About 26.1 cm.

*Inflorescence diameter*.—About 11.9 cm.

*Flower diameter*.—About 9 cm.

*Flower depth*.—About 4.6 cm.

*Petals*.—All petals are transformed into nectaries.

*Sepals*.—Quantity and arrangement: About five or occasionally, six, arranged in a single whorl. Length: About 5.2 cm. Width: About 5.1 cm. Shape: Broadly ovate; slightly to moderately concave. Apex: Obtuse. Base: Cuneate. Margin: Entire. Texture and luster, upper surface: Smooth, glabrous; matte. Texture and luster, lower surface: Smooth, glabrous; slightly glossy. Color: When opening, upper surface: Close to 76D; towards the margins, close to 186A and 186B; at the base, close to 145C. When opening, lower surface: Close to 72C; towards the apex and margins, close to 61A; at the base, close to 145B; lower sepals with irregular blotching, close to 155B. Fully opened, upper surface: Close to N155B; towards the margins and base, close to 76C and 76D; at the margins, close to N77B; towards the apex, tinged with close to 144B; at the base, close to 145C. Fully opened, lower surface: Close to 70B; towards the apex and margins, close to 71A and 71B; at the apex, tinged with close to 145A and 145B; at the base, close to 145B; lower sepals with irregular blotching, close to 155A and 155B.

*Flower bracts*.—Quantity per flower: Typically one or two. Length: About 7.3 cm. Width: About 6.1 cm. Shape: Broadly ovate to oblong. Apex: Acute to tri-lobed. Base: Truncate to cuneate. Margin: Entire and distally, serrate; coarsely undulate. Color, upper surface: Close to a blend of NN137A and 147A. Color, lower surface: Close to 147B.

*Peduncles*.—Length: About 16.4 cm. Diameter: About 5.5 mm to 6.5 mm. Aspect: About 22.5° from vertical. Strength: Strong. Texture and luster: Smooth, glabrous; slightly glossy. Color: Close to 144B; heavily covered with fine dots, close to 176A.

*Pedicels*.—Length: About 2.1 cm. Diameter: About 3 mm. Aspect: About 15° from peduncle axis. Strength: Moderately strong. Texture and luster: Smooth, glabrous; slightly to moderately glossy. Color: Close to 146D; moderately covered with fine dots, close to 176A.

*Reproductive organs*.—Stamens: Quantity per flower: About 100. Filament length: About 1.7 cm. Filament color: Close to 155A and 155B; distally, close to 186C and 186D. Anther shape: Double and broadly reniform; basifixed. Anther size: About 1.75 mm by 2.5 mm. Anther color: Close to 154C. Pollen amount: Sparse. Pollen color: Close to 4D. Pistils: Quantity per flower: About four to eight. Pistil length: About 1.3 cm. Stigma diameter: About 0.3 mm. Stigma shape: Club-shaped. Stigma color: Close to 157D. Style length: About 1.25 cm. Style color: Close to 64A. Ovary color: Close to 145C. Nectaries (transformed petals): Quantity per flower: About 14 to 19. Length: About 1.5 cm. Diameter: About 5 mm. Shape: Tubular, flattened; apices, obtuse. Texture and luster, inner and outer surfaces: Smooth, glabrous; matte. Color, immature, inner and outer surfaces: Close to 144B; distally, tinged with close to 183A. Color, mature, inner and outer surfaces: Close to 151C; distally, close to 153C and strongly tinged with close to 200A; at the apex, close to 183B; with subsequent development, color becoming closer to 153A strongly tinged with close to 200A. Seeds and fruits: To date, seed and fruit development have not been observed on plants of the new *Helleborus*.

Garden performance: Plants of the new *Helleborus* have been observed to have good garden performance and to tolerate rain, wind, high temperatures about 35° C. and to be suitable for USDA Hardiness Zones 5 through 9.

Pathogen & pest resistance: To date, plants of the new *Helleborus* have not been observed to be resistant to pathogens and pests common to *Helleborus* plants.

It is claimed:

1. A new and distinct *Helleborus* plant named 'HL 1056' as herein illustrated and described.

* * * * *